United States Patent [19]

Mohrs et al.

[11] Patent Number: 4,929,626
[45] Date of Patent: May 29, 1990

[54] α-SUBSTITUTED 4-(QUINOLIN-2-YL-METHOXY)PHENYLA-CETIC ACIDS AND ESTERS AND LIPOXYGENASE INHIBITION THEREWITH

[75] Inventors: Klaus Mohrs, Wuppertal; Siegfried Raddatz; Romanis Fruchtmann, both of Cologne; Christian Kohlsdorfer, Erfstadt; Reiner Müller-Peddinghaus, Bergisch-Gladbach, all of Fed. Rep. of Germany

[73] Assignee: Bayer Aktiengesellschaft, Leverkusen, Fed. Rep. of Germany

[21] Appl. No.: 336,974

[22] Filed: Apr. 12, 1989

[30] Foreign Application Priority Data

Apr. 29, 1988 [DE] Fed. Rep. of Germany ....... 3814504

[51] Int. Cl.$^5$ .................... C07D 215/14; A61K 31/47
[52] U.S. Cl. ...................... 514/311; 546/174
[58] Field of Search ........................ 546/174; 514/311

[56] References Cited

U.S. PATENT DOCUMENTS 4,642,347  2/1987  Krett et al. ........................ 546/181
4,661,499  4/1987  Young et al. ...................... 514/311

FOREIGN PATENT DOCUMENTS 0181568  5/1986  European Pat. Off. .

Primary Examiner—David B. Springer
Attorney, Agent, or Firm—Sprung Horn Kramer & Woods

[57] ABSTRACT

As lipoxygenase inhibitors, the novel α-substituted 4-(quinolin-2-yl-methoxy)phenyl-acetic acid and esters thereof of the formula

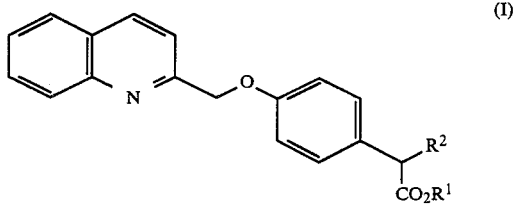

(I)

in which
 $R^1$ - stands for hydrogen, alkyl, arylalkyl, aryl or
 - for a group of the formula $$-CH_2-CO_2-R^3,$$

where
 $R^3$ - stands for hydrogen, alkyl, arylalkyl or aryl and
 $R^2$ - stands for hydrogen, alkyl, alkenyl or alkinyl,
and salts thereof.

11 Claims, No Drawings

α-SUBSTITUTED 4-(QUINOLIN-2-YL-METHOXY)PHENYLACETIC ACIDS AND ESTERS AND LIPOXYGENASE INHIBITION THEREWITH

The invention relates to new α-substituted 4-(quinolin-2-yl-methoxy)phenylacetic acids and their esters, processes for their preparation and their use in medicaments.

3-(Quinolin-2-yl-methoxy)phenylacetic acid and 2-[3-(quinolin-2-yl-methoxy)phenyl]propionic acid, and their methyl and ethyl esters with antiinflammatory and antiallergic action are described in EP-A 181,568.

New α-substituted 4-(quinolin-2-yl-methoxy)-phenylacetic acids and their esters of the general formula (I)

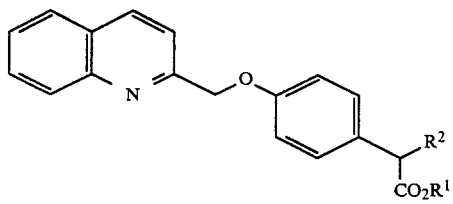

in which
$R^1$- stands for hydrogen, alkyl, arylalkyl, aryl or
- for a group of the formula $$-CH_2-CO_2-R^3,$$

where
$R^3$ - stands for hydrogen, alkyl, arylalkyl or aryl and
$R^2$ - stands for hydrogen, alkyl, alkenyl or alkinyl, and their salts, have been found.

In comparison to the meta-substituted compounds known from EP-A 181,568, the acids and esters of the general formula (I) according to the invention surprisingly have a higher pharmacological action, particularly after peroral administration.

Alkyl, in general, stands for a straight-chain or branched hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkenyl, in general, stands for a straight-chain or branched hydrocarbon radical having 2 to 12 carbon atoms and one or more, preferably one or two double bonds. The lower alkyl radical having 2 to about 8 carbon atoms and one double bond is preferred. An alkenyl radical having 2 to 6 carbon atoms and one double bond is particularly preferred. Examples which may be mentioned are allyl, propenyl, isopropenyl, butenyl, isobutenyl, pentenyl, isopentenyl, hexenyl, isohexenyl, heptenyl, isoheptenyl, octenyl and isooctenyl.

Alkinyl, in general, stands for a straight-chain or branched hydrocarbon radical having 2 to 10 carbon atoms and one or more, preferably one or two triple bonds. The lower alkinyl radical having 2 to 8 carbon atoms and having one triple bond is preferred. An alkinyl radical having 2 to 6 carbon atoms and one triple bond is particularly preferred. Examples which may be mentioned are ethinyl, propinyl, butinyl, pentinyl, isopentinyl, hexinyl and isohexinyl.

Aryl, in general, stands for an aromatic radical having 6 to about 12 carbon atoms. Preferred aryl radicals are phenyl, naphthyl and biphenyl.

Aralkyl, in general, stands for an aryl radical having 7 to 14 carbon atoms bonded via an alkylene chain. Aralkyl radicals having 1 to 6 carbon atoms in the aliphatic moiety and 6 to 12 carbon atoms in the aromatic moiety are preferred. Examples which may be mentioned are the following aralkyl radicals: benzyl, naphthylmethyl, phenethyl and phenylpropyl.

In the context of the present invention, physiologically acceptable salts are preferred. Physiologically acceptable salts of the compounds according to the invention may be salts of the substances according to the invention with mineral acids, carboxylic acids or sulphonic acids. For example, salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid are particularly preferred.

Salts in the context of the present invention are additionally salts of monovalent metals such as the alkali metals and those of ammonium. Sodium salts, potassium salts and ammonium salts are preferred.

Compounds of the general formula (I) are preferred in which
$R^1$ - stands for hydrogen, lower alkyl, benzyl or phenyl, or
- for a group of the formula $$-CH_2-CO_2-R^3,$$

where
$R^3$ - stands for hydrogen, lower alkyl, phenyl or benzyl and
$R^2$ - stands for hydrogen, lower alkyl, branched lower alkyl, lower alkenyl, branched lower alkenyl, lower alkinyl or branched lower alkinyl, and their salts.

Particularly preferred compounds of the general formula (I) are those in which
$R^1$ - stands for hydrogen, methyl, ethyl, benzyl or phenyl or
- for a group of the formula $$-CH_2-CO_2-R^3,$$

where
$R^3$ - stands for hydrogen, methyl, ethyl, phenyl or benzyl and
$R^2$- stands for hydrogen, methyl, ethyl, propyl, butyl, pentyl, hexyl, isopropyl, isobutyl, isopentyl, 2-butenyl, 2-pentenyl, allyl, 3,3-dimethylallyl, 2-butinyl, 2-propinyl, 3-pentinyl, 1-methyl-2-butinyl or 3-hexinyl, and their salts.

Examples which may be mentioned in detail are the following active compounds:
methyl 4-(quinolin-2-yl-methoxy)phenylacetate
methyl 2-[4-(quinolin-2-yl-methoxy)phenyl]propionate
methyl 2-[4-(quinolin-2-yl-methoxy)phenyl]butyrate
methyl 2-[4-(quinolin-2-yl-methoxy)phenyl]valerate
methyl 2-[4-(quinolin-2-yl-methoxy)phenyl]caproate
methyl 2-[4-(quinolin-2-yl-methoxy)phenyl]heptanoate methyl 2-[4-(quinolin-2-yl-methoxy)phenyl]-5-methyl-4-hexenoate
methyl E-2-[4-(quinolin-2-yl-methoxy)phenyl]-4-hexenoate
methyl 2-[4-(quinolin-2-yl-methoxy)phenyl]-4-hexinoate
methyl 2-[4-(quinolin-2-yl-methoxy)phenyl]isocaproate
methyl 2-[4-(quinolin-2-yl-methoxy)phenyl]isovalerate
methyl 2-[4-(quinolin-2-yl-methoxy)phenyl]-5-octinoate
4-(quinolin-2-yl-methoxy)phenylacetic acid
2-[4-(quinolin-2-yl-methoxy)phenyl]propionic acid
2-[4-(quinolin-2-yl-methoxy)phenyl]butyric acid
2-[4-(quinolin-2-yl-methoxy)phenyl]valeric acid
2-[4-(quinolin-2-yl-methoxy)phenyl]caproic acid
2-[4-(quinolin-2-yl-methoxy)phenyl]heptanoic acid
2-[4-(quinolin-2-yl-methoxy)phenyl]-5-methyl-4-hexenoic acid
E-2-[4-(quinolin-2-yl)methoxy)phenyl]-4-hexenoic acid
2-[4-(quinolin-2-yl-methoxy)phenyl]-4-hexinoic acid
2-[4-(quinolin-2-yl-methoxy)phenyl]isocaproic acid
2-[4-(quinolin-2-yl-methoxy)phenyl]isovaleric acid
methoxycarbonyl-methyl 2-[4-(quinolin-2-yl-methoxy)phenyl]caproate hydrochloride
benzyloxycarbonylmethyl 2-[4-(quinolin-2-yl-methoxy)phenyl]caproate
carboxymethyl 2-[4-(quinolin-2-yl-methoxy)phenyl]caproate
methoxycarbonylmethyl 4-(quinolin-2-yl-methoxy)phenylacetate
benzyloxycarbonylmethyl 4-(quinolin-2-yl-methoxy)phenylacetate
carboxymethyl 4-(quinolin-2-yl-methoxy)phenylacetate
sodium 2-[4-(quinolin-2-yl-methoxy)phenyl]caproate
ethyl 2-[4-(quinolin-2-yl-methoxy)phenyl]caproate In addition, a process for the preparation of the α-substituted 4-(quinolin-2-yl-methoxy)phenylacetic acids and esters of the general formula (I)

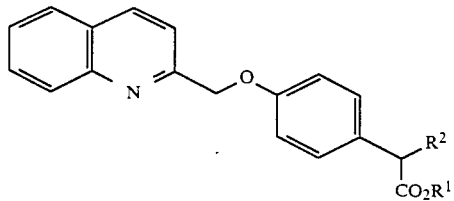

(I)

in which
$R^1$ and $R^2$ have the above-mentioned meaning, has been found, characterized in that [A] phenols of the general formula (II)

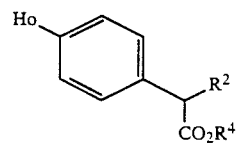

(II)

in which
$R^2$ has the above-mentioned meaning and
$R^4$ - stands for alkyl, arylalkyl or aryl, or
- for a group of the formula $$-CH_2-CO_2-R^5$$

where
$R^5$ - stands for alkyl, aralkyl or aryl, are reacted with 2-halogenomethylquinoline of the formula

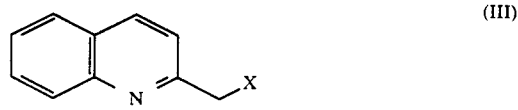

(III)

in which
X stands for halogen,
and in the case of the acids the esters are hydrolyzed, [B] esters of the general formula (IV)

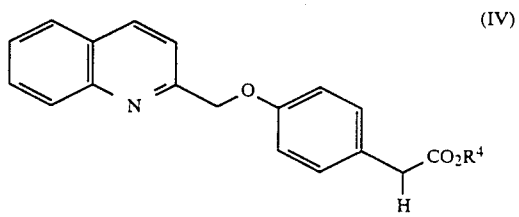

(IV)

in which
$R^4$ has the above-mentioned meaning, are alkylated with halides of the general formula (V)

$$R^6-X$$

(V)

in which
$R^6$ - stands for alkyl, alkenyl or alkinyl and
X - stands for halogen,
in the case of the preparation of acids, the esters are hydrolyzed and, if desired, the salts are prepared by addition of bases.

The process variants according to the invention can be illustrated by the following reaction schemes:

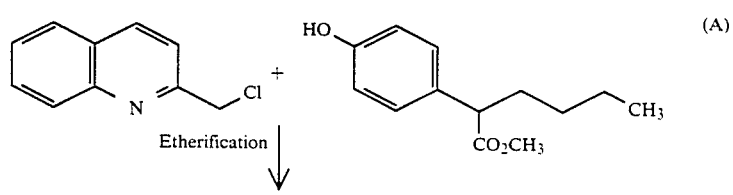

(A)

Etherification

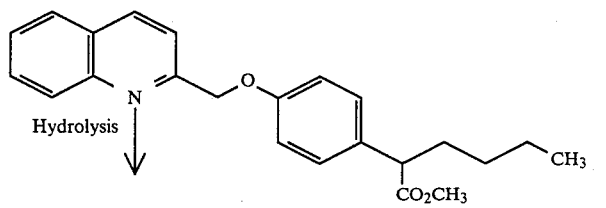

Hydrolysis ↓

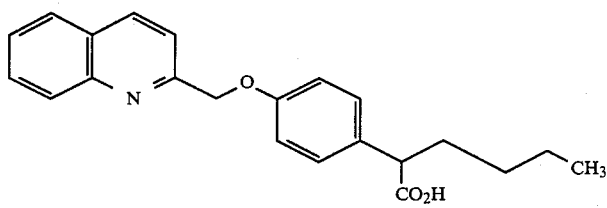

(B)

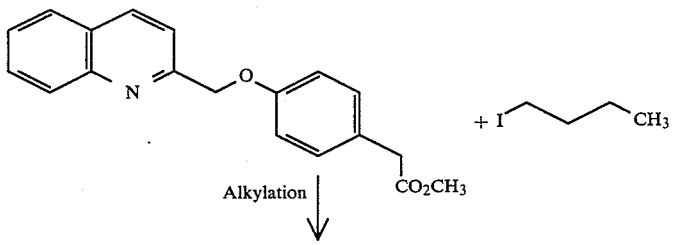

Alkylation ↓

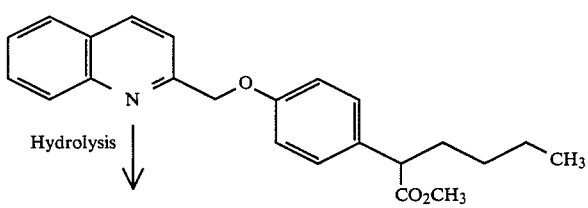

Hydrolysis ↓

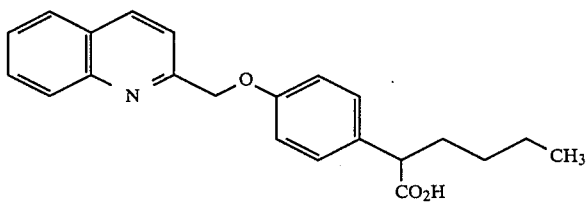

The etherification can be carried out in inert organic solvents, if desired in the presence of a base.

Solvents for the processes according to the invention can be inert organic solvents which do not change under the reaction conditions. These preferably include ethers such as, for example, dioxane, tetrahydrofuran or diethyl ether, halogenated hydrocarbons such as dichloromethane, trichloromethane, tetrachloromethane, 1,2-dichloroethane or trichloroethylene, hydrocarbons such as benzene, xylene, toluene, hexane, cyclohexane or mineral oil fractions, nitromethane, dimethylformamide, acetonitrile, acetone or hexamethylphosphoric triamide. It is also possible to employ mixtures of the solvents mentioned.

Inorganic or organic bases can be employed as bases for the process according to the invention. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or organic amines (trialkyl($C_1$–$C_6$)amines) such as triethylamine, or heterocycles such as pyridine, methylpiperidine, piperidine or morpholine.

It is also possible to employ alkali metals, such as sodium or its hydrides, such as sodium hydride, as bases.

The preparation of the compounds of the general formula (I) according to the invention is in general carried out in a temperature range from 0° C. to 150° C., preferably from 10° C. to 100° C.

The process variants according to the invention are in general carried out at atmospheric pressure. However, it is also possible to carry out the process at underpressure or overpressure (for example in the range from 0.5 to 5 bar).

In general, 0.5 to 5, preferably 1 to 2, moles of halide are employed, relative to 1 mole of the reaction partner. The base is in general employed in an amount of 0.5 to 5 moles, preferably from 1 to 3 moles, relative to the halide.

The alkylation of the C—H acidic compounds (formula IV) is in general carried out using alkyl halides in inert solvents in the presence of a base.

Depending on the nature of the alkylating agent, all inert organic solvents are suitable in this connection as solvents. These preferably include ethers such as diethyl ether, dioxane or tetrahydrofuran, or hydrocarbons such as benzene, toluene or xylene, or dimethylformamide or hexamethylphosphoric triamide, or mixtures of the solvents mentioned.

Suitable bases are the customary basic compounds. These preferably include alkali metal hydrides such as sodium hydride, alkali metal amides such as sodium amide or lithium diisopropylamide, alkali metal alkoxides such as sodium methoxide, sodium ethoxide, potassium methoxide, potassium ethoxide or potassium tert.butoxide, or organic amines such as trialkylamines, for example triethylamine, or organolithium compounds such as butyllithium or phenyllithium.

The preparation of the compounds according to the invention is in general carried out in the temperature range from 0° C. to 150° C., preferably from 10° C. to 100° C.

The process according to the invention is in general carried out at atmospheric pressure. However, it is also possible to carry out the process at underpressure or overpressure (for example in a range from 0.5 to 5 bar).

In general, 0.5 to 5, preferably 1 to 2, moles of halide are employed, relative to 1 mole of the reaction partner. The base is in general employed in an amount from 0.5 to 5 moles, preferably from 1 to 3 moles, relative to the halide.

The hydrolysis of the carboxylic acid esters is carried out by customary methods by treating the esters with customary bases in inert solvents, by means of which the initially resulting salts can be converted into the free carboxylic acids by treating with acid.

Suitable bases for hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium ethoxide, potassium methoxide or potassium tert.butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in the temperature range from 0° C. to +100° C., preferably from +20° C. to +80° C.

In general, the hydrolysis is carried out at atmospheric pressure. However, it is also possible to work at underpressure or at overpressure (for example from 0.5 to 5 bar).

In carrying out the hydrolysis, the base is in general employed in an amount from 1 to 3 moles, preferably from 1 to 1.5 moles, relative to 1 mole of the ester or the lactone. Molar amounts of reactants are particularly preferably used.

When carrying out the reaction, the salts of the compounds according to the invention are formed in the first step as intermediates which can be isolated. The acids according to the invention are obtained by treating the salts with customary inorganic acids. These preferably include mineral acids such as, for example, hydrochloric acid, hydrobromic acid, sulphuric acid or phosphoric acid. In this connection, it has proved advantageous in the preparation of the carboxylic acids to acidify the basic reaction mixture from the hydrolysis in a second step without isolation of the salts. The acids can then be isolated in a customary manner.

The esters of the general formula (I), in which $R^1$ stands for a group —$CH_2$—$CO_2R^3$ and $R^3$ has the above-mentioned meaning, can also be prepared from the corresponding acids of the general formula (I) by known methods by esterifying with α-hydroxyacetic acid esters or by alkylating esterification with α-halogenoacetic acid esters.

The acids, in turn, can be prepared, for example by hydrolytic or hydrogenolytic cleavage of the corresponding benzyl ester by known methods:

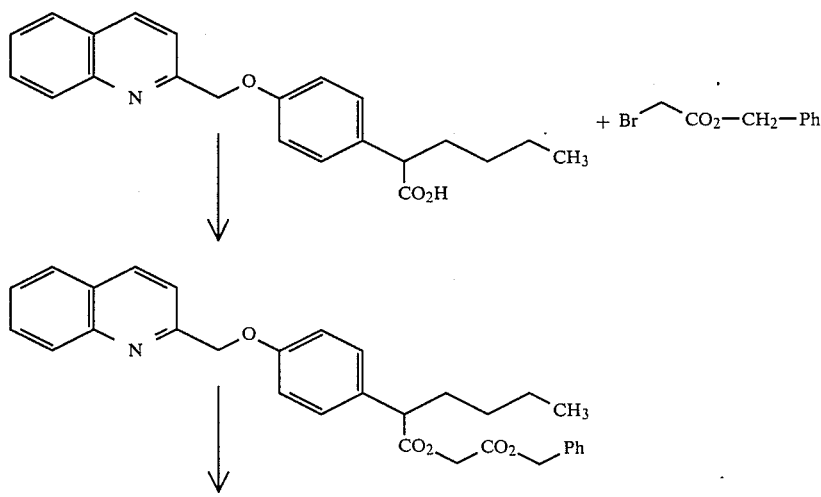

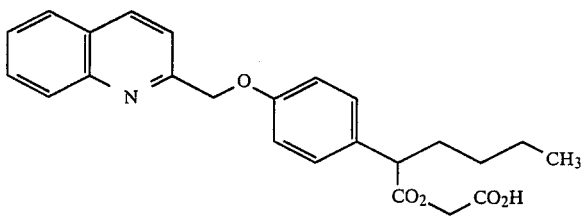

The phenols of the general formula (II) used as starting compounds are known per se and can be prepared from the corresponding ethers by cleaving off protective groups by customary methods [Th. Greene: "Protective Groups in Organic Synthesis, J. Wiley & Sons, 1981, New York.]

The esters of the general formula (IV) used as starting compounds are prepared from the known 4-hydroxyphenylacetic acid esters in an alkylation reaction with 2-chloromethylquinoline (analogous to process variant A).

The esterification of the carboxylic acids is carried out by customary methods by treating the acids with alkyl halides in inert solvents, if desired in the presence of a base.

Suitable bases are the customary organic amines. These preferably include alkylamines such as triethylamine, diisopropylamine, dicyclohexylamine and ethyldiisopropylamine.

Suitable solvents in this connection are all inert organic solvents. These preferably include ethers such as diethyl ether, dioxane or tetrahydrofuran, or hydrocarbons such as benzene, toluene or xylene, or dimethylformamide or mixtures of the solvents mentioned.

The preparation of the compounds according to the invention is in general carried out in a temperature range from 0° C. to 150° C., preferably from 10° C. to 100° C.

The process according to the invention is in general carried out at atmospheric pressure. However, it is also possible to carry out the process at underpressure or overpressure (for example in a range from 0.5 to 5 bar).

In general, 0.5 to 5, preferably 1 to 2, moles of halide are employed, relative to 1 mole of the reaction partner. The base is in general employed in an amount of 0.5 to 5 moles, preferably from 1 to 3 moles, relative to the halide.

In general, 0.01 to 1, preferably 0.05 to 0.5, mole of catalyst are employed, relative to 1 mole of reaction partner.

The hydrogenolytic cleavage of the benzyl ester is carried out by customary methods by hydrogenating the benzyl ester using hydrogen gas in an inert solvent in the presence of a catalyst.

Suitable catalysts are the customary metal catalysts which, if desired, are applied in variable concentrations to an inert support such as, for example, carbon. These preferably include palladium, nickel, platinum, particularly preferably 5 to 15% palladium on activated carbon.

Suitable solvents in this connection are all inert organic solvents. These preferably include ethers such as diethyl ether, dioxane or tetrahydrofuran, or hydrocarbons such as benzene, toluene or xylene, or alcohols such as methanol, ethanol or propanol, or lower-boiling esters such as ethyl acetate, or amines such as triethylamine, or mixtures of the solvents mentioned.

The preparation of the compounds according to the invention is in general carried out in a temperature range from 0° C. to 150° C., preferably from 10° C. to 100° C.

The process according to the invention is in general carried out using hydrogen at atmospheric pressure. However, it is also possible to carry out the process at overpressure (for example in a range from 1 to 10 bar).

The acids and esters according to the invention can be employed as active compounds in medicaments. The substances can act as inhibitors of enzymatic reactions in the context of arachidonic acid metabolism, in particular of lipoxygenase.

They are thus preferred for treatment and prophylaxis of diseases of the airways such as allergies/asthma, bronchitis, emphysema, shock lung, pulmonary hypertonia, inflammations/rheumatism and oedema, thromboses and thromboembolisms, ischaemia (peripheral, cardiac and cerebral circulatory disturbances), cardiac and renal infarcts, cardiac arrhythmias, angina pectoris, arteriosclerosis, in tissue transplants, dermatoses such as psoriasis, metastases and for cytoprotection in the gastrointestinal tract.

The new active compounds can be converted in a manner known per se using inert non-toxic, pharmaceutically suitable excipients or solvents into the customary formulations, such as tablets, capsules, dragees, pills, granules, aerosols, syrups, emulsions, suspensions and solutions. In this connection the therapeutically active compound should in each case be present in the preparation in a concentration of about 0.5 to 90% by weight, preferably 10 to 70% by weight, i.e. in amounts which are sufficient in order to achieve the dosage range indicated.

The formulations are prepared, for example, by extending the active compounds using solvents and/or excipients, if necessary using emulsifiers and/or dispersants, where, for example, in the case of the use of water as a diluent, organic solvents can be used as auxiliary solvents if necessary.

Examples of auxiliaries which may be mentioned are: water, non-toxic organic solvents such as paraffins (for example mineral oil fractions), vegetable oils (for example groundnut/sesame oil), alcohols (for example ethyl alcohol, glycerol), glycols (for example propylene glycol, polyethylene glycol), solid excipients, such as ground natural minerals (for example kaolins, argillaceous earths, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersants (for example lignin-sulphite waste liquors, methylcellulose, starch and polyvinylpyrrolidone) and lubricants (for example magnesium stearate, talc, stearic acid and sodium lauryl sulphate).

Administration may take place in a customary manner, preferably orally or parenterally, in particular perlingually or intravenously. In the case of oral administration, the tablets can, of course, also contain additions such as sodium citrate, calcium carbonate and dicalcium phosphate together with various additives, such as starch, preferably potato starch, gelatine and the like in addition to the excipients mentioned. Furthermore, lubricants, such as magnesium stearate, sodium lauryl sulphate and talc can additionally be used for tableting. In the case of aqueous suspensions and/or elixirs which are intended for oral use, various flavor-improvers or colorants may be added to the active compounds in addition to the above-mentioned auxiliaries.

In the case of parenteral administration, solutions of the active compounds can be employed using suitable liquid excipients.

In general, it has proved advantageous on intravenous administration to administer amounts of about 0.01 to 10 mg/kg, preferably about 0.01 to 5 mg/kg of body weight to attain effective results. On oral administration, the dosage is in general about 0.1 to 200 mg/kg, preferably 1 to 100 mg/kg of body weight.

In spite of this, it may be necessary to deviate from the amount mentioned, depending on the body weight or the type of administration route, on individual behavior towards the medicament, the nature of its formulation and the point in time or interval at which administration takes place. Thus, in some cases it may be sufficient to manage with less than the previously mentioned minimum amount, whereas in other cases the upper limit mentioned must be exceeded. In the case of administration of larger amounts, it may be advisable to divide these into a number of individual doses over the day.

The acids and esters according to the invention can be used both in human medicine and in veterinary medicine.

PREPARATION EXAMPLES

Example 1

Methyl 2-(4-methoxyphenyl)caproate

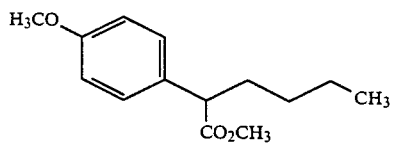

21.6 g of sodium hydride are suspended under protective gas in 1 L of dimethylformamide. 150 g of methyl 4-methoxyphenylacetate, dissolved in 200 ml of dimethylformamide, are slowly added dropwise with ice cooling. After evolution of hydrogen is complete, the mixture is stirred for 1 h at 25° C., 166 g of butyl iodide are subsequently added dropwise with ice cooling and the mixture is stirred for a further 16 h at 25° C. The solvent is evaporated off in vacuo, and the residue is taken up in water and extracted three times using ethyl acetate. After drying over sodium sulphate, the solvent is evaporated off and the residue is distilled in vacuo.

Yield: 127 g (65% of theory)
Boiling point: 101-105° C. (0.1 mm)

Example 2

Methyl 4-benzyloxyphenylacetate

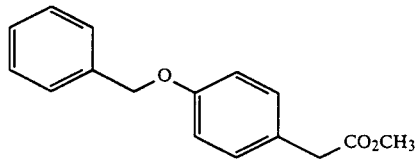

397 g of methyl 4-hydroxyphenylacetate and 330 g of potassium carbonate are stirred for 1 h at 50° C. in 2 1 L of dimethylformamide. 302 g of benzyl chloride are then added and the mixture is warmed to 50° C. for 15 h. After concentrating in vacuo, the residue is partitioned between water and ethyl acetate, and the organic phase is dried over sodium sulphate and concentrated. The product is recrystallized from methanol.

Yield: 511 g (83% of theory)
Melting point: 60° C.

Example 3

Methyl 2-(4-benzyloxyphenyl)caproate

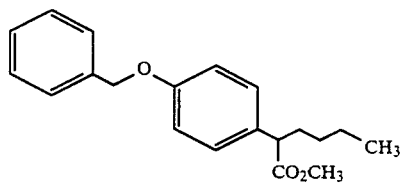

The preparation is carried out from 102 g of methyl 4-benzyloxyphenylacetate analogously to the directions of Example 1.

Yield: 106 g (85% of theory)
Boiling point: 180° C. (0.1 mm) (bulb tube)

Example 4

Methyl 2-(4-hydroxyphenyl)caproate

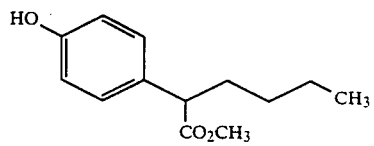

(a) 83 g of methyl 2-(4-methoxyphenyl)caproate are dissolved in 750 ml of dichloromethane. 360 ml of a 1 molar boron tribromide/dichloromethane solution are added dropwise at −75° C. under protective gas. After slowly warming, the mixture is stirred for 16 h at 25° C. After evaporating the solvent, 1 l of methanol and 250 ml of water are cautiously added to the residue and the mixture is warmed for 4 h under reflux. After concentrating, it is extracted three times using dichloromethane, the extract is evaporated and the residue is distilled in vacuo.

Yield: 58.5 g (75% of theory)
Boiling point: 130-135° C. (0.1 mm)

(b) 75 g of methyl 2-(4-benzyloxyphenyl)caproate are hydrogenated at atmospheric pressure in 900 ml of methanol and 100 ml of triethylamine with the addition of 1 g of palladium catalyst (5% strength on carbon). After absorption of the theoretical amount of hydrogen, the solution is filtered off from the catalyst and concentrated, and the residue is distilled.

Example 5

Methyl 4-(quinolin-2-yl-methoxy)phenylacetate

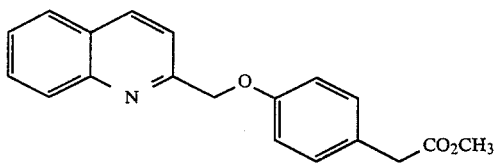

The preparation is carried out from 200 g of methyl 4-hydroxyphenylacetate and 214 g of 2-chloromethylquinoline analogously to the directions of Example 2.

Yield: 293 g (79% of theory)

Melting point: 71–73° C.

Example 6

Methyl 2-[4-(quinolin-2-yl-methoxy)phenyl]propionate

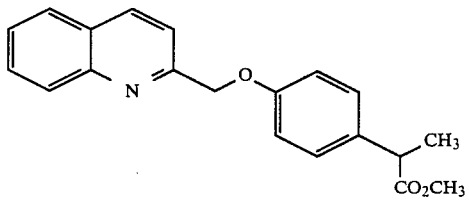

The preparation is carried out from 15.4 g of methyl 4-(quinolin-2-yl-methoxy)phenylacetate and 7.8 g of methyl iodide analogously to the directions of Example 1.

Yield: 7.8 g (49% of theory)

Melting point: 187–190° C. (0.5 × 1,5-naphlhalenedisulphonic acid salt).

Example 7

Methyl 2-[4-(quinolin-2-yl-methoxy)phenyl]butyrate

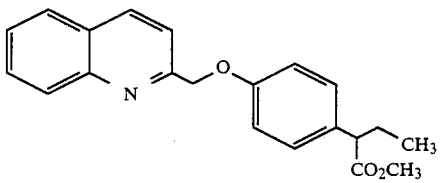

The preparation is carried out from 15.4 g of methyl 4-(quinolin-2-yl-methoxy)phenylacetate and 8.6 g of ethyl iodide analogously to the directions of Example 1.

Yield: 7.8 g (47% of theory)

Melting point: 53–56° C.

Example 8

Methyl 2-[4-(quinolin-2-yl-methoxy)phenyl]valerate

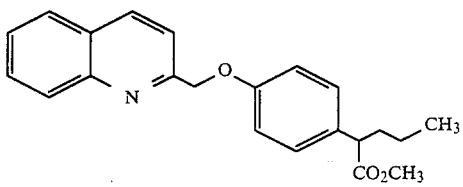

The preparation is carried out from 15.4 g of methyl 4-(quinolin-2-yl-methoxy)phenylacetate and 5.8 g of propyl bromide analogously to the directions of Example 1.

Yield: 7.9 g (45% of theory)

Melting point: 50–52° C.

Example 9

Methyl 2-[4-(quinolin-2-yl-methoxy)phenyl]caproate

The preparation is carried out from 56 g of methyl 2-(4-hydroxyphenyl)caproate and 44 g of 2-chloromethylquinoline analogously to the directions of Example 2.

Yield: 77 g (85% of theory)

Melting point: 144–146° C. (hydrochloride)

Example 10

Methyl 2-[4-(quinolin-2-yl-methoxy)phenyl]heptanoate

The preparation is carried out from 15.4 g of methyl 4-(quinolin-2-yl-methoxy)phenylacetate and 10.9 g of pentyl iodide analogously to the directions of Example 1.

Yield: 9.8 g (52% of theory)

Melting point: 41° C.

Example 11

Methyl 2-[4-(quinolin-2-yl-methoxy)phenyl]-5-methyl-4-hexenoate

The preparation is carried out from 15.4 g of methyl 4-(quinolin-2-yl-methoxy)phenylacetate and 8.2 g of 1-bromo-3-methyl-2-butene analogously to the directions of Example 1.

Yield: 16 g (86% of theory)
Melting point: 54–56° C.

Example 12

Methyl E-2-[4-(quinolin-2-yl-methoxy)phenyl]-4-hexenoate

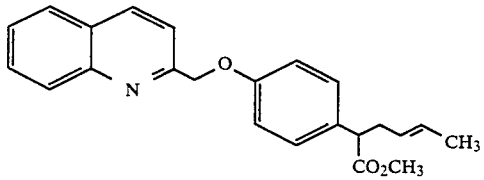

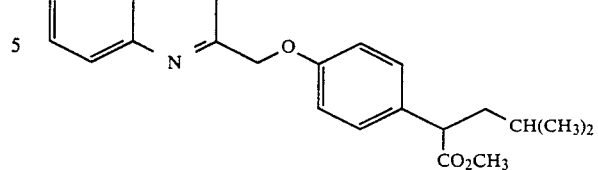

The preparation is carried out from 15.4 g of methyl 4-(quinolin-2-yl-methoxy)phenylacetate and 5.1 g of isobutyl chloride analogously to the directions of Example 1.

Yield: 8.0 g (44% of theory)
Melting point: 62° C.

Example 15

Methyl 2-[4-(quinolin-2-yl-methoxy)phenyl]isovalerate

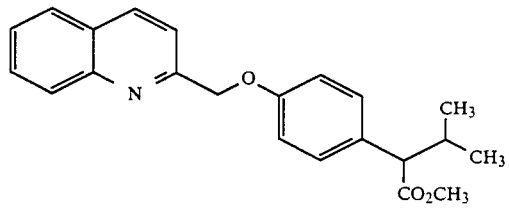

The preparation is carried out from 15.4 g of methyl 4-(quinolin-2-yl-methoxy)phenylacetate and 7.4 g of trans-1-bromo-2-butene analogously to the directions of Example 1.

Yield: 12.2 g (68% of theory)
Melting point: 47° C.

Example 13

Methyl 2-[4-(quinolin-2-yl-methoxy)phenyl]-4-hexinoate

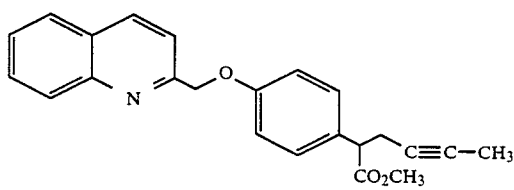

The preparation is carried out from 15.4 g of methyl 4-(quinolin-2-yl-methoxy)phenylacetate and 7.32 g of 1-bromo-2-butine analogously to the directions of Example 1.

Yield: 10.2 g (57% of theory)
Melting point: 53° C.

Example 14

Methyl 2-[4-(quinolin-2-yl-methoxy)phenyl]isocaproate

The preparation is carried out from 15.4 g of methyl 4-(quinolin-2-yl-methoxy)phenylacetate and 9.4 g of isopropyl iodide analogously to the directions of Example 1.

Yield: 13 g (74% of theory)
Melting point: 69–71° C.

Example 16

4-(Quinolin-2-yl-methoxy)phenylacetic acid

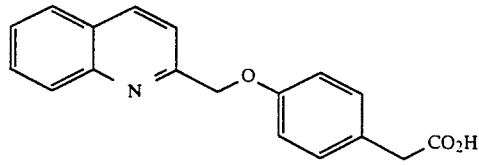

49 g of methyl 4-(quinolin-2-yl-methoxy)phenylacetate are stirred for 5 h at 25° C. in 250 ml of methanol and 192 ml of 1 normal sodium hydroxide solution. The mixture is acidified using concentrated hydrochloric acid with ice cooling. The precipitated product is filtered off with suction, dried and recrystallized from acetone.

Yield: 44.6 g (95% of theory)
Melting point: 158–159° C.

Example 17

2-[4-(Quinolin-2-yl-methoxy)phenyl]propionic acid

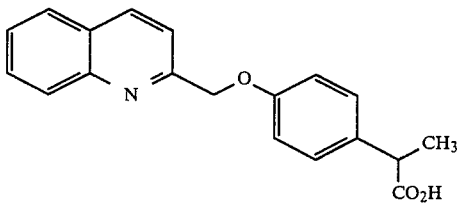

The preparation is carried out from 5.3 g of methyl 2-[4-(quinolin-2-yl-methoxy)phenyl]propionate analogously to the directions of Example 16.
Yield: 4 g (78% of theory)
Melting point: 145° C.

Example 18

2-[4-(Quinolin-2-yl-methoxy)phenyl]butyric acid

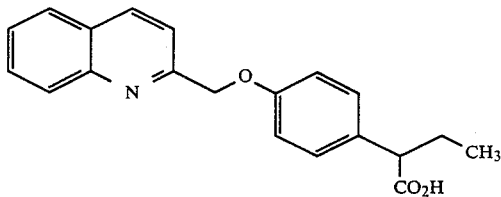

The preparation is carried out from 5.1 g of methyl 2-[4-(quinolin-2-yl-methoxy)phenyl]butyrate analogously to the directions of Example 16.
Yield: 3.6 g (73% of theory)
Melting Point: 153° C.

Example 19

2-[4-(Quinolin-2-yl-methoxy)phenyl]valeric acid

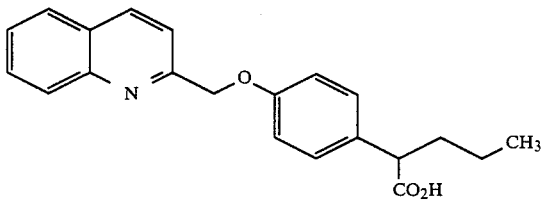

The preparation is carried out from 5.3 g of methyl 2-14-(quinolin-2-yl-methoxy)phenyl]valerate analogously to the directions of Example 16.
Yield: 3.1 g (61% of theory)
Melting point: 135° C.

Example 20

2-[4-(Quinolin-2-yl-methoxy)phenyl]caproic acid

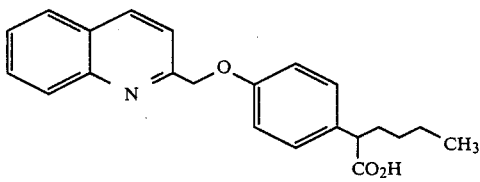

The preparation is carried out from 91 g of methyl 2-[4-(quinolin-2-yl-methoxy)phenyl]caproate analogously to the directions of Example 16.
Yield: 64.5 g (74% of theory)
Melting point: 131–132° C.

Example 21

2-[4-(Quinolin-2-yl-methoxy)phenyl]heptanoic acid

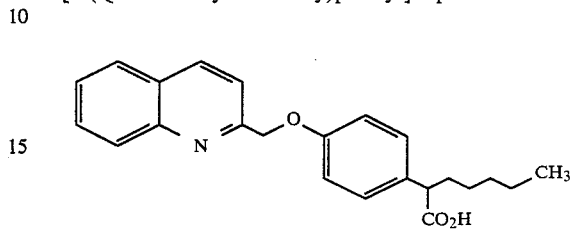

The preparation is carried out from 7.2 g of methyl 2-[4-(quinolin-2-yl-methoxy)phenyl]heptanoate analogously to the directions of Example 16.
Yield: 5.5 g (76% of theory)
Melting point: 75° C.

Example 22

2-[4-(Quinolin-2-yl-methoxy)phenyl]-5-methyl-4-hexenoic acid

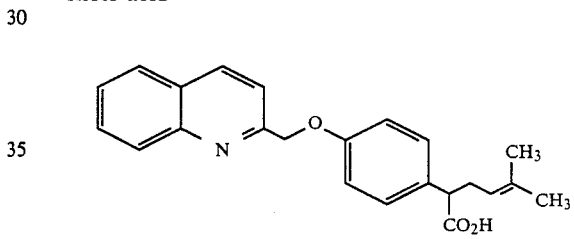

The preparation is carried out from 13.7g of methyl 2-[4-(quinolin-2-yl-methoxy)phenyl]-5-methyl-4-hexenoate analogously to the directions of Example 16.
Yield: 8.4 g (64% of theory)
Melting point: 114° C.

Example 23

E-2-[4-(Quinolin-2-yl-methoxy)phenyl]-4-hexenoic acid

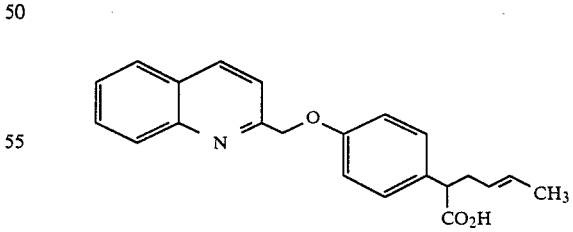

The preparation is carried out from 9.7 g of methyl E-2-[4-(quinolin-2-yl-methoxy)phenyl]-4-hexenoate analogously to the directions of Example 16.
Yield: 9.1 g (98% of theory)
Melting point: 137° C.

Example 24

2-[4-(Quinolin-2-yl-methoxy)phenyl]-4-hexinoic acid

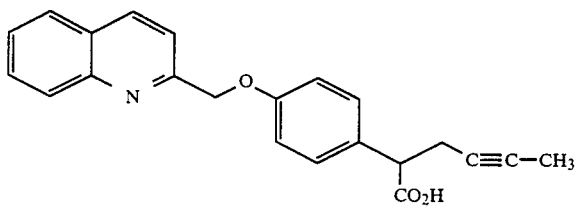

The preparation is carried out from 6.7 g of methyl 2-[4-(quinolin-2-yl-methoxy)phenyl]-4-hexinoate analogously to the directions of Example 16.
Yield: 4.0 g (62% of theory)
Melting point: 177° C.

Example 25

Methyl 2-[4-(quinolin-2-yl-methoxy)phenyl]isocaproic acid

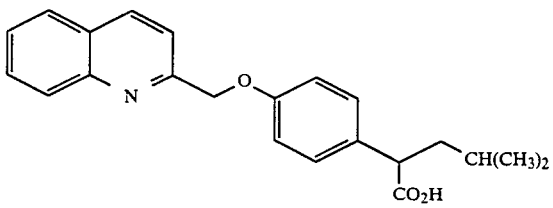

The preparation is carried out from 5.8 g of methyl 2-[4-(quinolin-2-yl-methoxy)phenyl]isocaproate analogously to the directions of Example 16.
Yield: 4.2 g (75% of theory)
Melting point: 117° C.

Example 26

2-[4-(Quinolin-2-yl-methoxy)phenyl]isovaleric acid

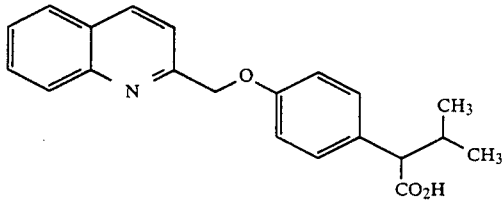

The preparation is carried out from 11.7 g of methyl 2-[4-(quinolin-2-yl-methoxy)phenyl]isovalerate analogously to the directions of Example 16.
Yield: 10.6 g (95% of theory)
Melting point: 173° C.

Example 27

Methoxycarbonylmethyl 2-[4-(quinolin-2-yl-methoxy)-phenyl]caproate hydrochloride

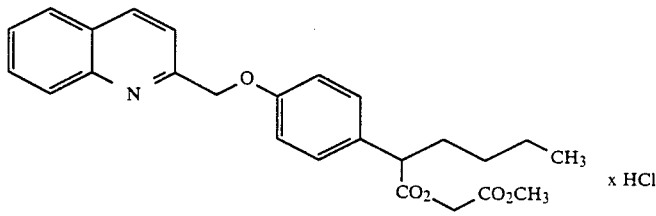

1.7 g of 2-[4-(quinolin-2-yl-methoxy)phenyl]-caproic acid, 0.84 g of methyl bromoacetate and 1 g of dicyclohexylamine are heated to boiling for 16 h in 30 ml of tetrahydrofuran. After cooling to 0° C., the mixture is filtered off from precipitated salt and the solvent is evaporated in vacuo. The residue is taken up in ether and an ethereal hydrogen chloride solution is added. The product precipitates out, is filtered off and dried.
Yield: 2 g (90% of theory)
Melting point: 70–73° C.

Example 28

Benzyloxycarbonylmethyl 2-[4-(quinolin-2-yl-methoxy)phenyl]caproate

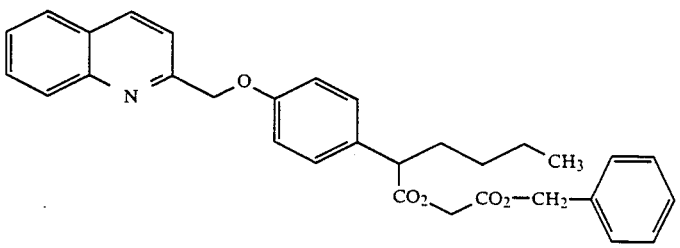

The preparation is carried out from 7 g of 2-[4-(quinolin-2-yl-methoxy)phenyl]caproic acid and 5 g of benzyl bromoacetate analogously to the directions of Example 27.

Yield: 9.5 g (95% of theory)

Melting point: 68–69° C.

Example 29

Carboxymethyl 2-[4-(quinolin-2-yl-methoxy)phenyl]caproate

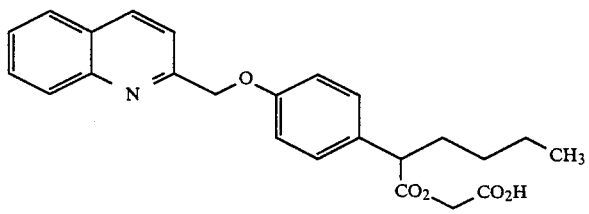

8.5 g of benzyloxycarbonylmethyl 2-[4-(quinolin-2-yl-methoxy)phenyl]caproate are dissolved in 150 ml of ethyl acetate and 15 ml of triethylamine, 0.9 g of palladium catalyst (10% strength on carbon) is added and the mixture is hydrogenated at 25° C. at atmospheric pressure. After absorption of the theoretical amount of hydrogen, the catalyst is filtered off. After concentrating in vacuo, the residue is partitioned between ethyl acetate/water, and the organic phase is dried and concentrated.

Yield: 4.3 g (62% of theory)
Melting point: 142–144° C. (hydrochloride)

Example 30

Methoxy-carbonylmethyl 4-(quinolin-2-yl-methoxy)phenylacetate

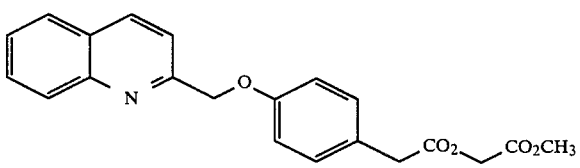

The preparation is carried out from 7.3 g of 4-(quinolin-2-yl-methoxy)phenylacetic acid and 4.2 g of methyl bromoacetate analogously to the directions of Example 27.

Yield: 7.1 g (78% of theory)

Melting point: 82–83.5° C.

Example 31

Benzyloxycarbonylmethyl 4-(quinolin-2-yl-methoxy)phenylacetate

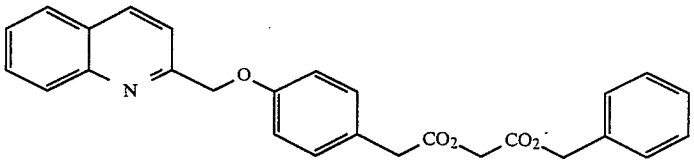

The preparation is carried out from 7.3 g of 4-(quinolin-2-yl-methoxy)phenylacetic acid and 6.3 g of benzyl bromoacetate analogously to the directions of Example 27.

Yield: 6.3 g (57% of theory)

Melting point: 60–62° C.

Example 32

Carboxymethyl 4-(quinolin-2-yl-methoxy)phenylacetate

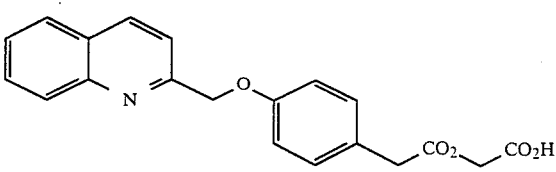

The preparation is carried out from 5.7 g of benzyloxycarbonylmethyl 4-(quinolin-2-yl-methoxy)phenylacetate analogously to the directions of Example 29.

Yield: 3.7 g (81% of theory)
Melting point: 148–149° C.

ExampLe 33

Sodium 2-[4-(quinolin-2-yl-methoxy)phenyl]caproate

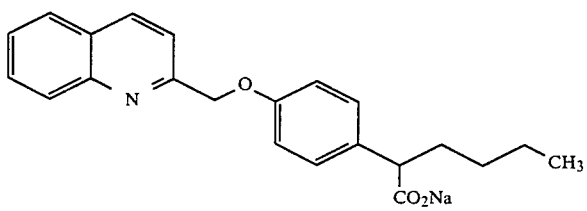

3.5 g of 2-[4-(quinolin-2-yl-methyloxy)phenyl]caproic acid are dissolved in 40 ml of methanol. After addition of 10 ml of 1-normal sodium hydroxide solution (equimolar amount), the mixture is concentrated to dryness and dried in vacuo at 100° C.

Yield: quantitative
Melting point: 187–193° C.

Example 34

Ethyl 2-[4-(quinolin-2-yl-methoxy)phenyl]caproate

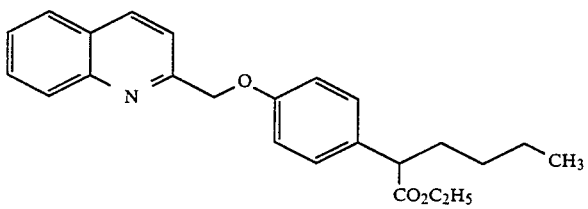

The preparation is carried out analogously to the directions of Example 2 from 36 g of chloromethylquinoline and 40 g of ethyl 2-(4-hydroxyphenyl)caproate Yield: 52 g (81% of theory)
Melting point: 48° C.

USE EXAMPLE

Example 35

In comparison with the known substance 2-[3-(1-hydroxyhexyl)phenoxymethyl]quinoline [compare EP-A 110,405]), the compounds according to the invention show a considerably stronger pharmacological activity.

The pharmacological activity data of the substances according to the invention are determined by the following method:

As a measure of the lipoxygenase inhibition, the release of leukotriene $B_4$ ($LTB_4$) by polymorphonuclear rat leukocytes (PMN) was determined after addition of substances and Ca ionophore by means of reverse phase HPLC according to Borgeat, P. et al., Proc. Nat. Acad. Sci. 76, 2148–2152 (1979). The in vivo activity of the compounds was determined using the mouse ear inflammation model according to Young, J. M. et al., J. of Investigative Dermatology 82, 367–371 (1984).

The values obtained by these tests for some compounds according to the invention are shown by way of example in Tables 1 and 2:

TABLE 1

| Example | Lipoxygenase inhibition IC$_{50}$ (μM) |
|---|---|
| No. 20 | 0.055 |
| No. 27 | 0.063 |
| No. 29 | 0.055 |
| 2-[[3-(1-hydroxyhexyl)-phenoxy]methyl]quinoline | 0.2 |

TABLE 2

| Example | Inhibition of inflammation % 100 mg/kg p.o. |
|---|---|
| No. 10 | 61 |
| No. 12 | 59 |
| No. 20 | 68 |
| No. 22 | 77 |
| No. 29 | 72 |
| 2-[[3-(1-hydroxyhexyl)-phenoxy]methyl]quinoline | 24 |

It will be understood that the specification and examples are issustrative but not limitative of the present invention and that other embodiments within the spirit and scope of the invention will suggest themselves to those skilled in the art.

We claim:

1. An α-substituted 4-(quinolin-2-yl-methoxy)-phenylacetic acid or ester thereof of the formula

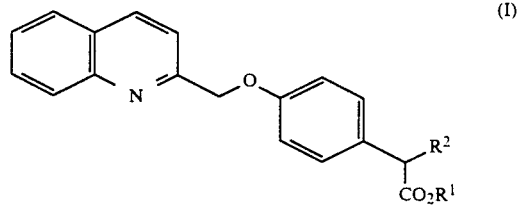

(I)

in which
R$^1$ - stands for hydrogen, alkyl, arylalkyl, aryl or
- for a group of the formula $-CH_2-CO_2-R^3$, where
R$^3$ - stands for hydrogen, alkyl, arylalkyl or aryl and
R$^2$ - stands for hydrogen, alkyl, alkenyl or alkinyl, or a pharmaceutically acceptable salt thereof.

2. An α-substituted 4-(quinolin-2-yl-methoxy)-phenylacetic acid or ester or salt thereof according to claim 1, in which R¹ - stands for hydrogen, lower alkyl, benzyl or phenyl, or
- for a group of the formula $$-CH_2-CO_2-R^3,$$

where
R³ - stands for hydrogen, lower alkyl, phenyl or benzyl and
R² - stands for hydrogen, lower alkyl, branched lower alkyl, lower alkenyl, branched lower alkenyl, lower alkinyl or branched lower alkinyl. and their salts.

3. An α-substituted 4-(quinolin-2-yl-methoxy)-phenylacetic acid or ester or salt thereof according to claim 1, in which
R¹ - stands for hydrogen, methyl, ethyl, benzyl or phenyl, or
- for a group of the formula $$-CH_2-CO_2-R^3,$$

where
R³ - stands for hydrogen, methyl, ethyl, phenyl or benzyl and
R² - stands for hydrogen, methyl, ethyl, propyl, butyl, pentyl, hexyl, isopropyl, isobutyl, isopentyl, 2-butenyl, 2-pentenyl, allyl, 3,3-dimethylallyl, 2-butinyl, 2-propinyl, 3-pentinyl, 1-methyl-2-butinyl or 3-hexinyl.

4. A compound according to claim 1, wherein such compound is 2-[4-(quinolin-2-yl-methoxy)phenyl]caproic acid of the formula

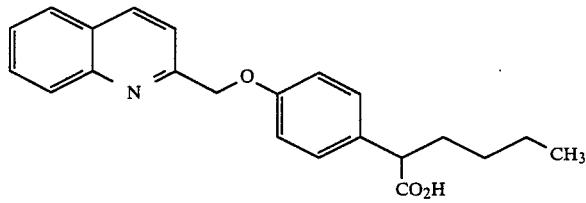

or a salt thereof.

5. A compound according to claim 1, wherein such compound is 2-[4-(quinolin-2-yl-methoxy)phenyl]-5-methyl-4-hexenoic acid of the formula

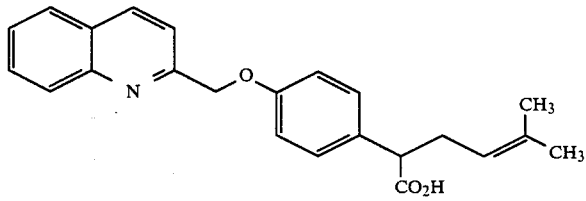

or a salt thereof.

6. A compound according to claim 1, wherein such compound is 2-[4-(quinolin-2-yl-methoxy)phenyl]isovaleric acid of the formula

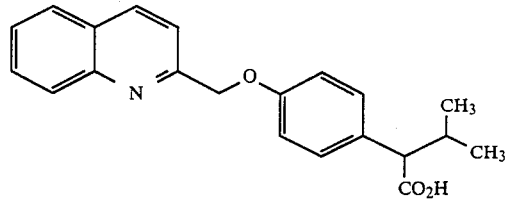

or a salt thereof.

7. A compound according to claim 1, wherein such compound is carboxymethyl 2-[4-(quinolin-2-yl-methoxy)phenyl]caproate of the formula

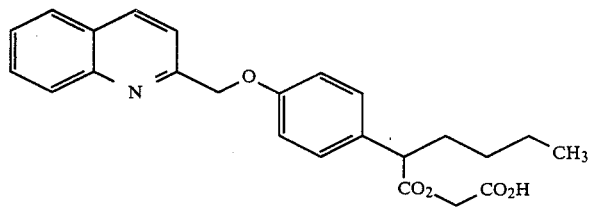

or a salt thereof.

8. A lipoxygenase inhibiting composition comprising an amount effective therefor of a compound or salt according to claim 1 and a diluent.

9. A unit dose of a composition according to claim 8, in the form of a tablet, capsule or ampule.

10. A method of inhibiting lipoxygenase in a patient in need thereof which comprises administering to such patient an amount effective therefor of a compound or salt according to claim 1.

11. The method according to claim 10, wherein such compound is
2-[4-(quinolin-2-yl-methoxy)phenyl]caproic acid,
2-[4-(quinolin-2-yl-methoxy)phenyl]-5-methyl-4-hexenoic acid,
2-[4-(quinolin-2-yl-methoxy)phenyl]isovaleric acid, or
carboxymethyl-2-[4-(quinolin-2-yl-methoxy)phenyl]caproate.

* * * * *